United States Patent [19]

Kadowaki et al.

[11] Patent Number: 5,450,466
[45] Date of Patent: Sep. 12, 1995

[54] RADIOGRAPHIC APPARATUS HAVING A C-SHAPED ARM FOR SUPPORTING AN X-RAY TUBE AND AN IMAGE RECEIVING UNIT

[75] Inventors: Toshio Kadowaki, Kyoto; Shojiro Yamaguchi, Uji; Hajime Takemoto, Muko; Toshiaki Nakamura, Kyoto, all of Japan

[73] Assignee: Shimadzu Corporation, Kyoto, Japan

[21] Appl. No.: 219,288

[22] Filed: Mar. 28, 1994

[30] Foreign Application Priority Data

Mar. 31, 1993 [JP] Japan .................................. 5-098478

[51] Int. Cl.6 .............................................. H05G 1/02
[52] U.S. Cl. .................................... 378/194; 378/197; 378/189
[58] Field of Search ................ 378/193, 194, 196, 197, 378/198, 189, 190, 204, 210; 250/522.1

[56] References Cited

U.S. PATENT DOCUMENTS

| | | | |
|---|---|---|---|
| 4,802,197 | 1/1989 | Juergens | 378/194 |
| 4,816,617 | 3/1989 | Valosen | 378/194 |

*Primary Examiner*—David P. Porta
*Assistant Examiner*—Don Wong
*Attorney, Agent, or Firm*—Nikaido, Marmelstein, Murray & Oram

[57] ABSTRACT

A radiographic apparatus includes a C-shaped arm for supporting an X-ray tube at one end thereof and an image receiving unit at the other end, and an arm holder for slidably supporting the C-shaped arm for rotation about a center of an arc thereof. The arm holder has a hollow shaft supported therein to extend substantially parallel to an axis of the center of the arc, and a take-up drum supported on the hollow shaft. A drum drive device is operable in response to rotation of the C-shaped arm to rotate the take-up drum. A plurality of cables are connected to the X-ray tube and the image receiving unit, respectively. The cables are gathered into a bundle adjacent the X-ray tube or the image receiving unit, the bundle being guided by an outer periphery of the C-shaped arm to be wound on the take-up drum. The bundle further extends through the take-up drum and the hollow shaft into and then out of the hollow shaft.

6 Claims, 9 Drawing Sheets

RADIOGRAPHIC APPARATUS HAVING A C-SHAPED ARM FOR SUPPORTING AN X-RAY TUBE AND AN IMAGE RECEIVING UNIT

BACKGROUND OF THE INVENTION

1. Field of the Invention

This invention relates to a radiographic apparatus, which may be suspended from the ceiling, for use in surgical diagnosis or in diagnosis of the circulatory system, and having a C-shaped arm for supporting an X-ray tube and an image receiving unit. More particularly, the invention relates to a technique of wiring a plurality of electric cables connected to the X-ray tube and image receiving unit disposed at opposite ends of the C-shaped arm.

2. Description of the Related Art

Figure 1:
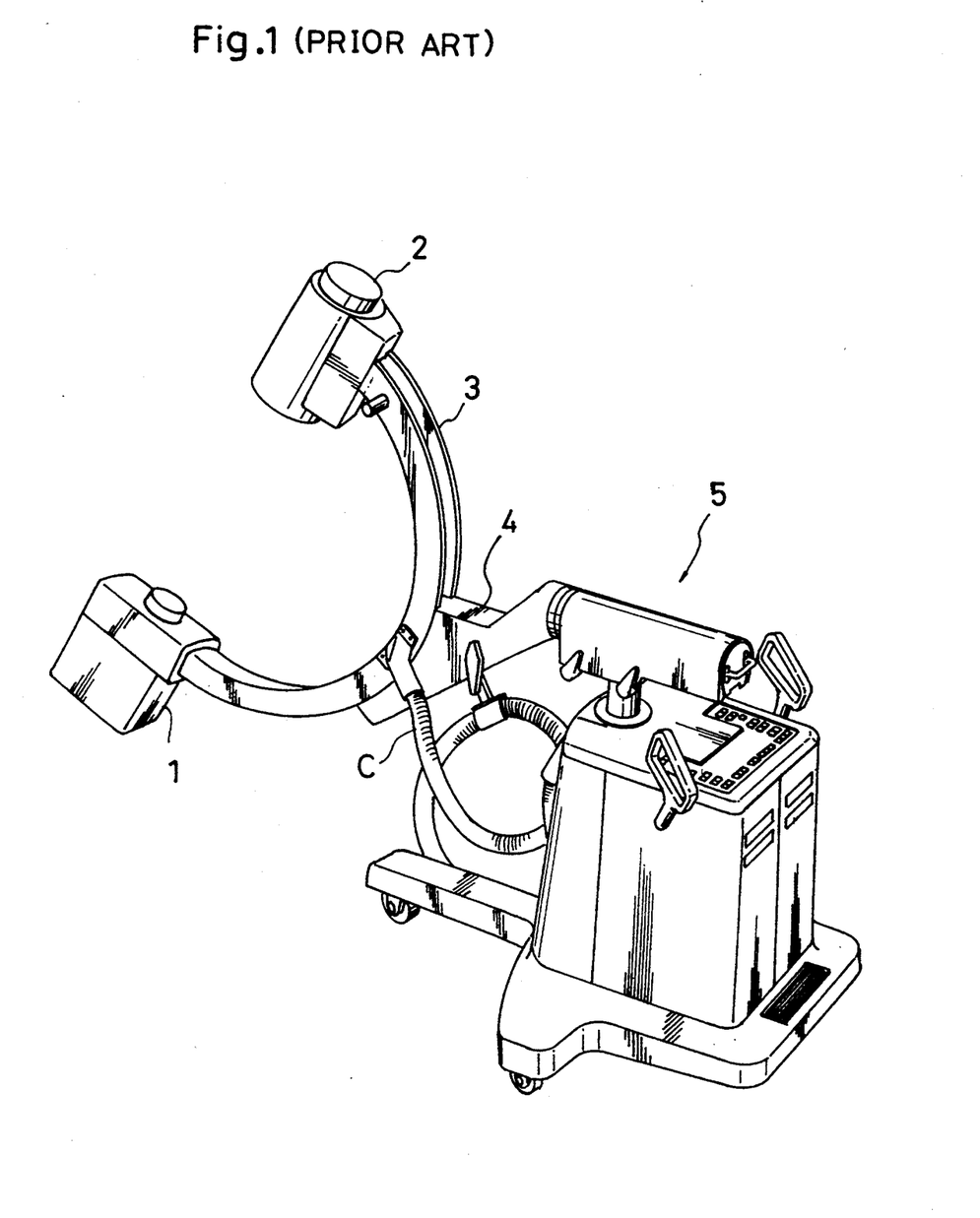
FIG. 1 is an overall perspective view of a conventional radiographic apparatus.

FIG. 1 shows an example of conventional radiographic apparatus for use in surgical diagnosis. This apparatus includes an X-ray tube 1 attached to one end of a C-shaped arm 3, and an image receiving unit 2 attached to the other end of the C-shaped arm 3. The image receiving unit 2 includes an X-ray image intensifier and a television camera. The C-shaped arm 3 is slidably supported by an arm holder 4 for rotation about the center of the arc. The center of the arc is set to an examinee lying on a bed or the like, and the C-shaped arm 3 is rotated to varied angles without moving the examinee. X rays are emitted from the X-ray tube 1 to sites of the examinee to be inspected. The image receiving unit 2 picks up images of the X rays transmitted through the examinee.

The above apparatus has a plurality of cables connected to the X-ray tube 1 and image receiving unit 2 at the opposite ends of the C-shaped arm 3, respectively. Such cables are passed through hollow interiors of the C-shaped arm 3 and bundled into an electric cable C adjacent a middle position of the C-shaped arm 3. The cable C extends outward from a lateral surface of the C-shaped arm 3, reaching a main body 5 of the apparatus, in a loose, relaxed form necessary to accommodate movement of the C-shaped arm 3.

However, since the C-shaped arm 3 is movable according to varied examining conditions, slack portions of the cable C extending from the lateral surface of the C-shaped arm 3 to the main body 5 of the apparatus may encumber treating or control operations, and may interfere with an operation to drive the C-shaped arm 3. Particularly when slack portions of the cable C are present above the examinee, these portions could sag into contact with the examinee or with personnel engaged in a surgical operation such as doctors and operators, thereby impairing sanitation.

SUMMARY OF THE INVENTION

This invention has been made having regard to the state of the art noted above, and its primary object is to provide a radiographic apparatus having an electric cable connected to a main body of the apparatus without slacking outside a C-shaped arm.

The above object is fulfilled, according to this invention, by a radiographic apparatus comprising:

a C-shaped arm for supporting an X-ray tube at one end thereof and an image receiving unit at the other end;

an arm holder for slidably supporting the C-shaped arm for rotation about a center of an arc thereof;

a hollow shaft supported in the arm holder to extend substantially parallel to an axis of the center;

a take-up drum supported on the hollow shaft;

a drum drive device responsive to rotation of the C-shaped arm to rotate the take-up drum; and a plurality of cables connected to the X-ray tube and the image receiving unit, respectively, and gathered into a bundle adjacent one of the X-ray tube and the image receiving unit, the bundle being guided by an outer periphery of the C-shaped arm to be wound on the take-up drum, and extending through the take-up drum and the hollow shaft into and then out of the hollow shaft.

When the C-shaped arm is rotated, the drum drive device rotates the take-up drum to wind up the bundled cable guided by the outer periphery of the C-shaped arm or to allow the cable wound on the take-up drum to be drawn therefrom. This ensures that the cable does not become slack outside the C-shaped arm. Thus, there is no possibility of the cable interfering with an operation to drive the C-shaped arm or impairing sanitation during a surgical operation.

In a preferred embodiment of this invention, the hollow shaft is rotatably supported in the arm holder, the take-up drum being rotatable with the hollow shaft about a common axis, the drum drive device including a pulley rotatable with the take-up drum about the common axis, and a wire wound on the pulley and having opposite ends thereof guided by the outer periphery of the C-shaped arm and secured to opposite ends of the C-shaped arm, the wire being wound on the pulley with a radius corresponding to a winding radius of the bundle on the take-up drum.

In the above construction, a wire is wound on a pulley rotatable on a common axis with the take-up drum, the wire having opposite ends thereof secured to opposite ends of the C-shaped arm. Thus, the wire is movable with rotation of the C-shaped arm, to rotate the pulley. The take-up drum is rotated with the pulley to wind up the bundled cable on the take-up drum. The cable wound on the take-up drum is drawn therefrom when the C-shaped arm rotated in the opposite direction. Consequently, the C-shaped arm is rotatable without slacking the cable, whereby the cable does not interfere with a surgical operation or impair sanitation during the surgical operation.

In another preferred embodiment of this invention, the hollow shaft is rotatably supported in the arm holder, the take-up drum being rotatable with the hollow shaft about a common axis, and defining a cable guide groove having a width corresponding to a thickness of the bundle to take up the bundle in overlapping coils, the drum drive device including a pulley rotatable with the take-up drum about the common axis, and a wire having one end thereof secured to the pulley and the other end guided by the outer periphery of the C-shaped arm and secured to one end of the C-shaped arm, the pulley defining a wire guide groove in form of a conical spiral so that the wire is wound on the pulley with radii corresponding to radii of the bundle wound in overlapping coils on the take-up drum.

In the above construction, when the C-shaped arm is rotated, the bundled cable is pulled to rotate the take-up drum. The pulley begins to rotate with rotation of the take-up drum, to take up the wire. At this time, the take-up drum rotates under control of the wire, whereby the cable is drawn, without slacking, from the take-up drum. When the C-shaped arm is rotated in the opposite direction, the wire rotates the take-up drum to wind up the cable on the take-up drum in a sequence reversed from the above. At this time, the wire is wound on the pulley with radii corresponding to radii of the bundled cable wound on the take-up drum and fitting in the cable guide groove. Thus, the cable is wound on the take-up drum, without slacking, by a length corresponding to a rotating angle of the C-shaped arm.

In a further preferred embodiment of the invention, the hollow shaft is rotatably supported in the arm holder, the take-up drum being rotatable with the hollow shaft about a common axis, the drum drive device including a sprocket rotatable with the take-up drum about the common axis, and a chain engaged with the sprocket and having opposite ends thereof guided by the outer periphery of the C-shaped arm and secured to opposite ends of the C-shaped arm, the chain being wound on the sprocket with a radius corresponding to a winding radius of the bundle on the take-up drum.

In this construction, the drum drive device includes a chain movable with rotation of the C-shaped arm, and a sprocket engaged with the chain, to transmit rotation of the C-shaped arm to the take-up drum reliably. This allows the bundled cable to be wound on the take-up drum or unwound therefrom reliably.

In a still further embodiment of this invention, the hollow shaft is fixed to the arm holder, the take-up drum being rotatably supported on the hollow shaft, and defining a cable guide groove having a width corresponding to a thickness of the bundle and a cable introducing section formed between the cable guide groove and the hollow shaft for winding the bundle a plurality of times to take up the bundle in overlapping coils, the drum drive device including a pulley rotatable with the take-up drum about a common axis, and a wire having one end thereof secured to the pulley and the other end guided by the outer periphery of the C-shaped arm and secured to one end of the C-shaped arm, the pulley defining a wire guide groove in form of a conical spiral so that the wire is wound on the pulley with radii corresponding to radii of the bundle wound in overlapping coils in the take-up drum.

The bundled cable is wound plural times between the cable guide groove in rotation and the hollow shaft remaining stationary. This provides an allowance for cable length, whereby the cable is free from a load such as torsional stress during rotation of the take-up drum. Consequently, the cable may be wound and unwound without being damaged.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DETAILED DESCRIPTION OF THE PREFERRED EMBODIMENTS

Preferred embodiments of this invention will be described in detail hereinafter with reference to the drawings.

First Embodiment

Figure 2:
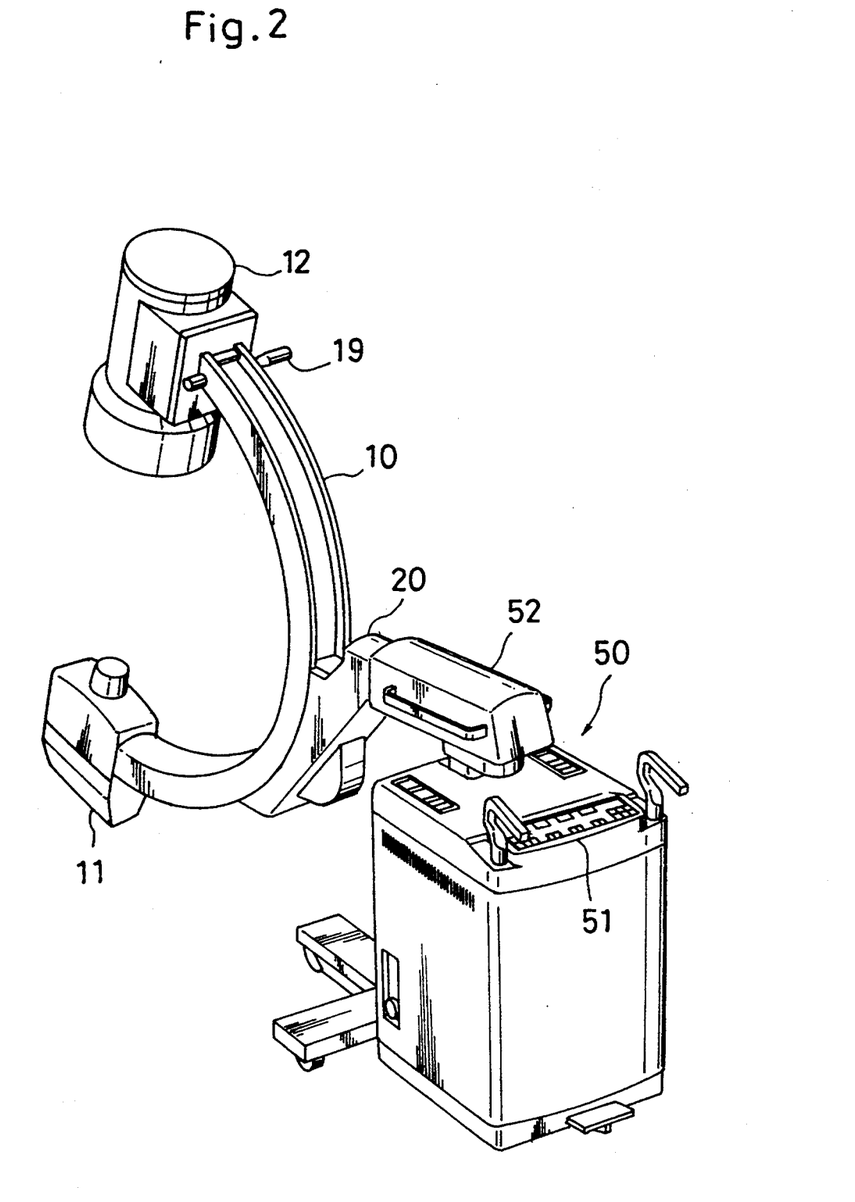
FIG. 2 is an overall perspective view of a radiographic apparatus in a first embodiment of this invention.

FIG. 2 is an overall perspective view of a radiographic apparatus in a first embodiment of this invention. This radiographic apparatus includes an X-ray tube 11 for emitting X rays to an examinee not shown, an image receiving unit 12 having an X-ray image intensifier and a television camera for picking up images of the X rays transmitted through the examinee, a C-shaped arm 10 supporting the X-ray tube 11 and image receiving unit 12 at opposite ends thereof as opposed to each other, an arm holder 20 for slidably supporting the C-shaped arm 10 to be rotatable about the center of its arc, and a main apparatus body 50. The main body 50 houses various components including an X-ray controller connected to the X-ray tube 11, and includes a control panel 51 and an arm bearing 52 arranged on an upper surface thereof. The arm bearing 52 is vertically movable relative to the main body 50, and supports the arm holder 20 to be pivotable about a horizontal axis. The C-shaped arm 10 includes a handle 19 projecting from an upper position thereof. The user may grip the handle 19 and move the C-shaped arm 10 to vary an X-ray emitting direction from the X-ray tube 11 to the image receiving unit 12 to a selected angle. That is, the C-shaped arm 10 is set to place the center of the arc in the examinee lying on a bed or the like, and is rotated to a selected angle without moving the examinee. X rays are emitted from the X-ray tube 11 to a site of the examinee requiring inspection. The image receiving unit 12 detects an image of the X rays transmitted through the examinee, and outputs corresponding image signals. The image signals are applied to a television monitor not shown, to display an X-ray penetration image.

Details of the above construction will be described next with reference to FIGS. 3 through 6.

Figure 3:
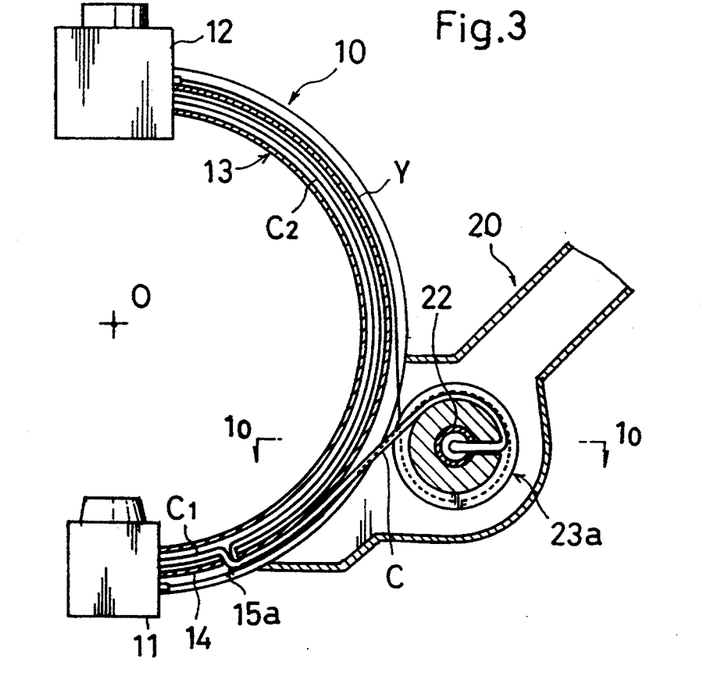
FIG. 3 is a view in vertical section of a principal portion of the first embodiment.
Figure 4:
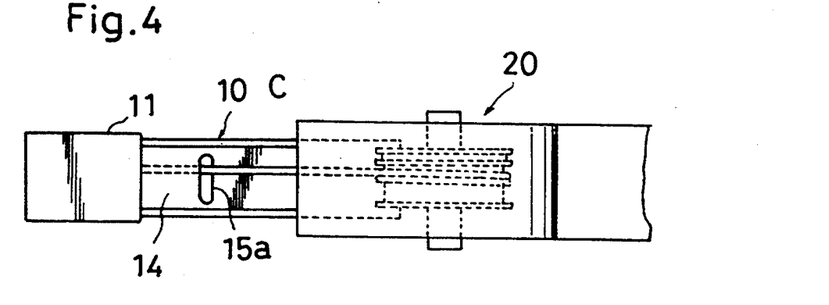
FIG. 4 is a bottom view of the portion shown in FIG. 3.
Figure 5:
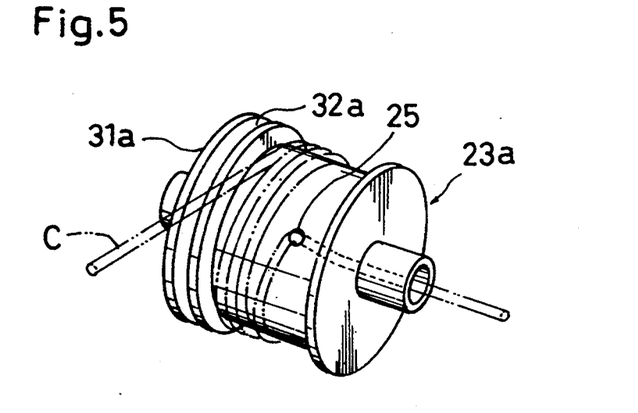
FIG. 5 is a perspective view of a take-up drum.
Figure 6:
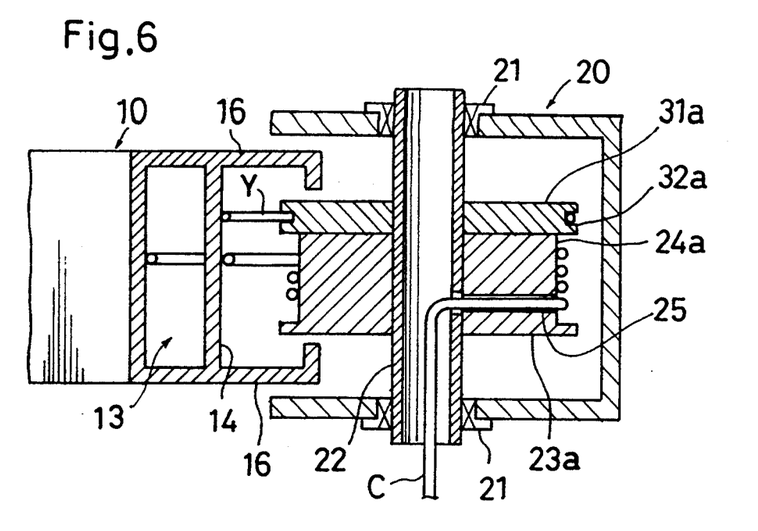
FIG. 6 is a section taken on line $1_0$—$1_0$ of FIG. 3.

As shown in FIGS. 3 and 6, the C-shaped arm 10 is formed of a C-shaped square pipe 14 including a pair of flanges 16 opposed to each other and extending peripherally thereof to define a rectangular hollow cross section. A plurality of cables C1 and C2 connected to the X-ray tube 11 and image receiving unit 12, respectively, extend through an interior space 13 of the square pipe 14. As shown in FIG. 4, the square pipe 14 of the C-shaped arm 10 has a guide slot 15a formed in an outer peripheral surface thereof adjacent the X-ray tube 11. This guide slot 15a is located in a position not to move past a take-up drum 23a described later, when the C-shaped arm 10 is rotated to a maximum degree counterclockwise. The guide slot 15a has a width approximately corresponding to the diameter of a bundled cable C, and is elongated in a direction traversing a direction in which the cable C is taken up in helical form on the take-up drum 23a. The cables C1 and C2 are bundled through the guide slot 15a into the cable C to be led out of the interior space 13 of the square pipe 14. The cable C led out is guided, along with a wire Y described later, to extend circumferentially of the square pipe 14 between the pair of flanges 16. The flanges 16 have free edges bent inward to ensure that the cable C and wire Y follow the outer periphery of the square pipe 14.

The arm holder 20 includes a hollow shaft 22 rotatably supported therein through a pair of bearings 21, and extending parallel to an axis of the center of the arc, i.e. the center of rotation, of the C-shaped arm 10. The take-up drum 23a is supported on the hollow shaft 22 to be rotatable therewith. The take-up drum 23a has a cable guide groove 24a formed peripherally thereof for guiding the cable C wound thereon. The take-up drum 23a interposes between the pair of flanges 16 of the C-shaped arm 10, so that the cable guide groove 24a lies in the close vicinity of the outer periphery of the square pipe 14. A through hole 25 is formed between the hollow shaft 22 and cable guide groove 24a for leading the cable C wound along the cable guide groove 24a to the interior of the hollow shaft 22.

According to the above construction, the cable C1 connected to the X-ray tube 11 and the cable C2 connected to the image receiving unit 12 extend along arcuate passages through the interior space 13 of the square pipe 14 of the C-shaped arm 10. The cables C1 and C2 are bundled into the cable C adjacent the X-ray tube 11. The cable C is led out through the guide slot 15a, guided by the outer periphery of the square pipe 14, passed through a space between the square pipe 14 and take-up drum 23a, and wound on the take-up drum 23a. The cable C wound on the take-up drum 23a is led by way of the through hole 25 to the interior of the hollow shaft 22. The cable C further extends through one end of the hollow shaft 22 to the main body 50. Thus, the cable C led out of the C-shaped arm 10 is taken up, without slacking, on the take-up drum 23a.

A pulley 31a is fixed to one side of the take-up drum 23a to be rotatable therewith. The pulley 31a has a wire guide groove 32a formed peripherally thereof for winding the wire Y. The wire guide groove 32a has such an outside diameter that the wire Y is wound on the pulley 31a with the same radius as the cable C is wound on the take-up drum 23a. One end of the wire Y wound on the pulley 31a is guided by the outer periphery of the square pipe 14 of the C-shaped arm 10 and secured to the end of the square pipe 14 where the X-ray tube 11 is mounted. The other end of the wire Y is guided in the opposite direction by the outer periphery of the square pipe 14 and secured to the end thereof supporting the image receiving unit 12. The pulley 31a and wire Y constitute a drum drive device.

Operation of this embodiment will be described next with reference to FIGS. 7 and 8.

Figure 7:
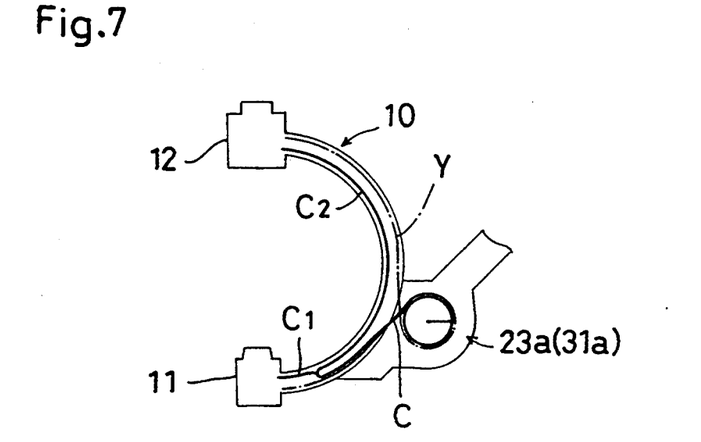
FIG. 7 is an explanatory view of operation of the first embodiment.

Assume that the C-shaped arm 10 is manually rotated clockwise from the position shown in FIG. 7, in which the opposite ends of the C-shaped arm 10 are vertically opposed to each other. As the C-shaped arm 10 is rotated clockwise, the end of the wire Y adjacent the X-ray tube 11 is pulled in the same clockwise direction. The resulting movement of the wire Y rotates the pulley 31a counterclockwise. That is, the pulley 31a is rotated counterclockwise by an amount corresponding to an amount of rotation of the C-shaped arm 10. The take-up drum 23a is rotated in unison with the pulley 31a, thereby allowing the cable C to be unwound from the take-up drum 23a by a length corresponding to the amount of rotation of the C-shaped arm 10. At this time, the C-shaped arm 10 is drawn, without slacking, from the take-up drum 23a by a length corresponding to a rotating angle of the C-shaped arm 10 since the winding radius of the cable C on the take-up drum 23a is equal to that of the wire Y on the pulley 31a.

Figure 8:
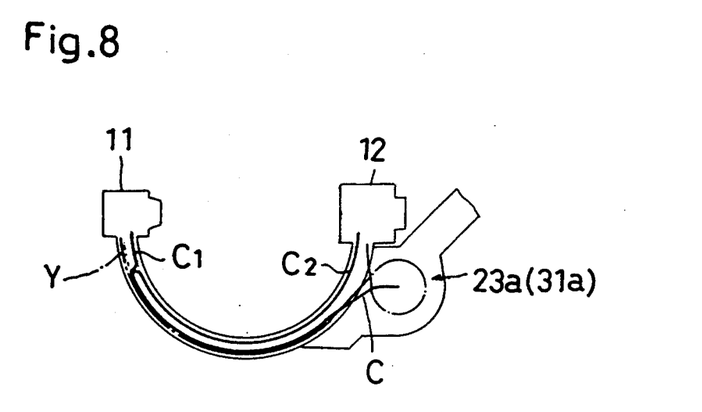
FIG. 8 is another explanatory view of operation of the first embodiment.

FIG. 8 shows a case reversed from the above, in which the C-shaped arm 10 is rotated counterclockwise from a position having the opposite ends thereof in horizontal alignment. In this instance, the take-up drum 23a is rotated clockwise by the opposite movement of the wire Y, to take up the cable C around the cable guide groove 24a.

Second Embodiment

Figure 9:
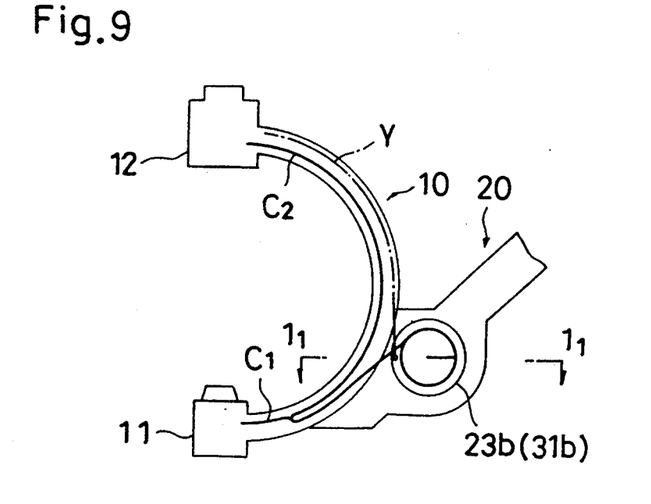
FIG. 9 is a view in vertical section of a principal portion of a second embodiment.

FIG. 9 is a view in vertical section of a principal portion of a radiographic apparatus in a second embodiment. In FIG. 9, like reference numerals are used to identify like parts in FIGS. 2 through 8 which are the same as in the first embodiment and will not be described again.

Figure 10:
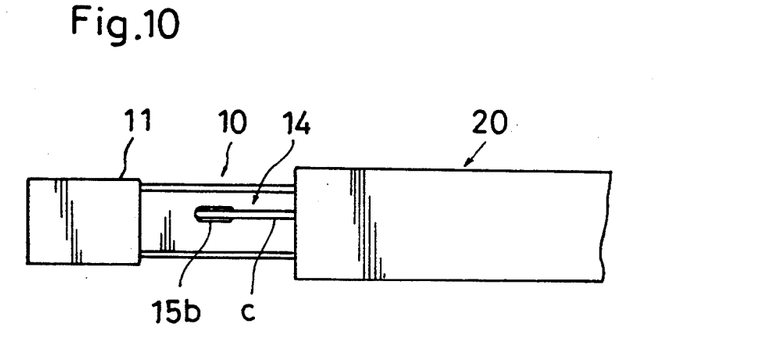
FIG. 10 is a bottom view of the portion shown in FIG. 9.
Figure 11:
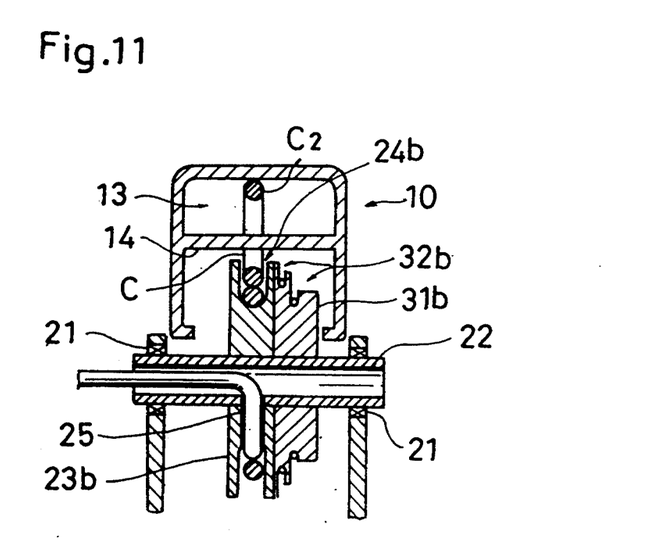
FIG. 11 is a section taken on line $1_1$—$1_1$ of FIG. 9.

The second embodiment will be described with reference to FIGS. 9 through 11.

As in the first embodiment, the square pipe 14 of the C-shaped arm 10 has a guide slot 15b formed in an outer peripheral surface thereof adjacent the X-ray tube 11. As distinct from the first embodiment, the bundled cable C is wound in radially overlapping coils on a take-up drum 23b described later. In line with this cable winding mode, the guide slot 15b has a width approximately corresponding to the diameter of the bundled cable C, but is elongated toward a cable guide groove 24b formed in the take-up drum 23b to allow the cable C to proceed straight to the cable guide groove 24b. The cables C1 and C2 are bundled through the guide slot 15b into the cable C to be led out of the interior space 13 of the square pipe 14.

The take-up drum 23b is supported on the hollow shaft 22 to be rotatable therewith. The cable guide groove 24b, which has a width corresponding to the thickness of the bundled cable C, is formed deep in the periphery of the take-up drum 23b for winding the cable C in radially overlapping coils thereon.

A pulley 31b is fixed to one side of the take-up drum 23b to be rotatable therewith. The pulley 31b has a wire guide groove 32b formed peripherally thereof for winding the wire Y. The wire guide groove 32b is in the form of a conical spiral, so that the wire Y is wound on the pulley 31b with the same radius as the cable C is wound on the take-up drum 23b, which radius is continuously variable with rotation of the take-up drum 23b and pulley 31b.

The wire Y is secured at one end thereof to a peripheral position of the wire guide groove 32b of the pulley 31b. The other end of the wire Y is guided by the outer periphery of the square pipe 14 and secured to the end thereof supporting the image receiving unit 12. The pulley 31b and wire Y constitute a drum drive device.

Figure 12A:
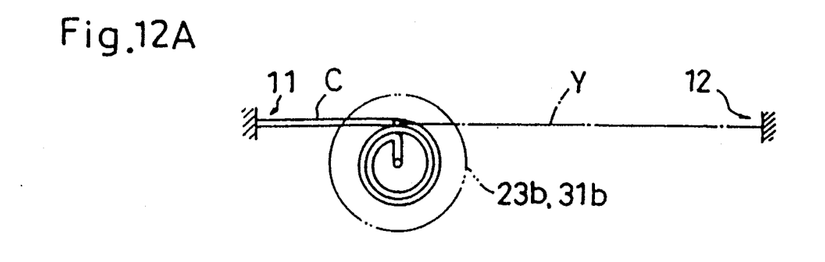
FIGS. 12A–B are explanatory views of operation of the second embodiment.

Operation of the second embodiment will be described next with reference to FIGS. 12 through 14.

FIGS. 12A through 14A are views in development showing winding states of the cable C and wire Y. FIGS. 12B through 14B are views showing positions of the C-shaped arm 10 corresponding to the winding states of FIGS. 12A through 14A, respectively.

Figure 12B:
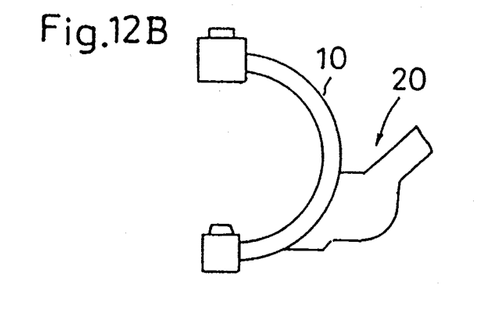
Figure 13A:
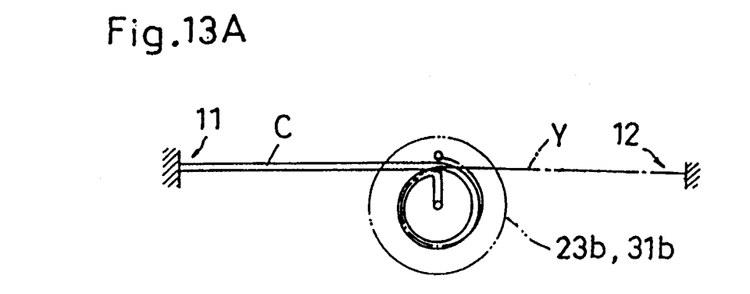
FIGS. 13A–B are other explanatory views of operation of the second embodiment.

When the opposite ends of the C-shaped arm 10 are vertically opposed to each other as shown in FIG. 12B, the cable C is already wound on the take-up drum 23b. That is, as shown in FIG. 12A, the X-ray tube supporting end of the C-shaped arm 10 lies adjacent the take-up drum 23b, with the cable C wound on the take-up drum 23b. The image receiving unit supporting end of the C-shaped arm 10 is remote from the pulley 31b, with the wire Y extending therebetween.

Figure 13B:
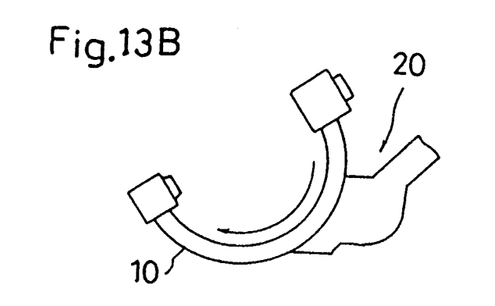
Figure 14A:
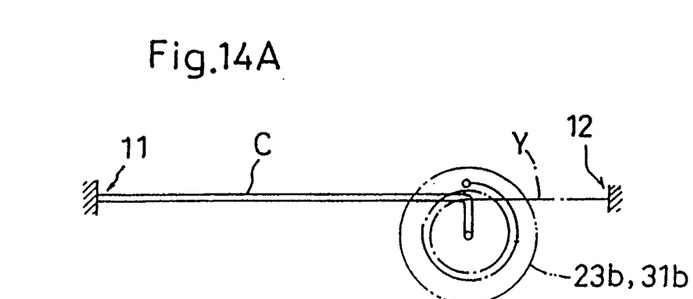
FIGS. 14A–B are further explanatory views of operation of the second embodiment.

Assume that, as shown in FIG. 13B, the C-shaped arm 10 is manually rotated clockwise from the above position. Then, as shown in FIG. 13A, the cable C is pulled by movement of the X-ray tube supporting end. As a result, the take-up drum 23b is rotated counterclockwise by an amount corresponding to an amount of movement of the X-ray tube supporting end. Simultaneously with the rotation of the take-up drum 23b, the pulley 31b begins to rotate, thereby to take up the wire Y thereon. Since the wire Y extends tight between the image receiving unit supporting end and pulley 31b, the cable C is drawn from the take-up drum 23b rotating in a controlled manner at this time. Thus, the cable C is drawn, without slacking, from the take-up drum 23b.

Figure 14B:
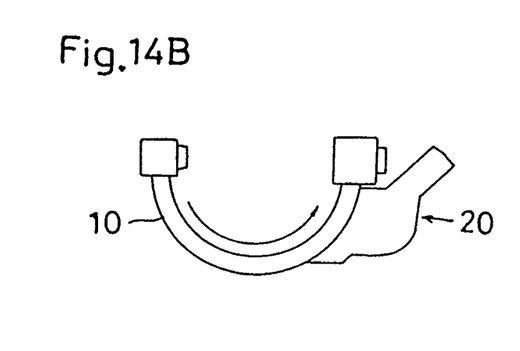

FIG. 14B shows a position of the C-shaped arm 10 in which the opposite ends thereof are horizontally opposed to each other. When the C-shaped arm 10 is rotated counterclockwise from this position, a sequence reversed from the above takes place, and the wire Y rotates the take-up drum 23b clockwise to take up the cable C thereon.

At this time, the cable C is taken up, without slacking, on the take-up drum 23b by a length corresponding to a rotating angle of the C-shaped arm 10 since the winding radius of the cable C on the take-up drum 23b is equal to that of the wire Y on the pulley 31b.

Third Embodiment

Figure 15:
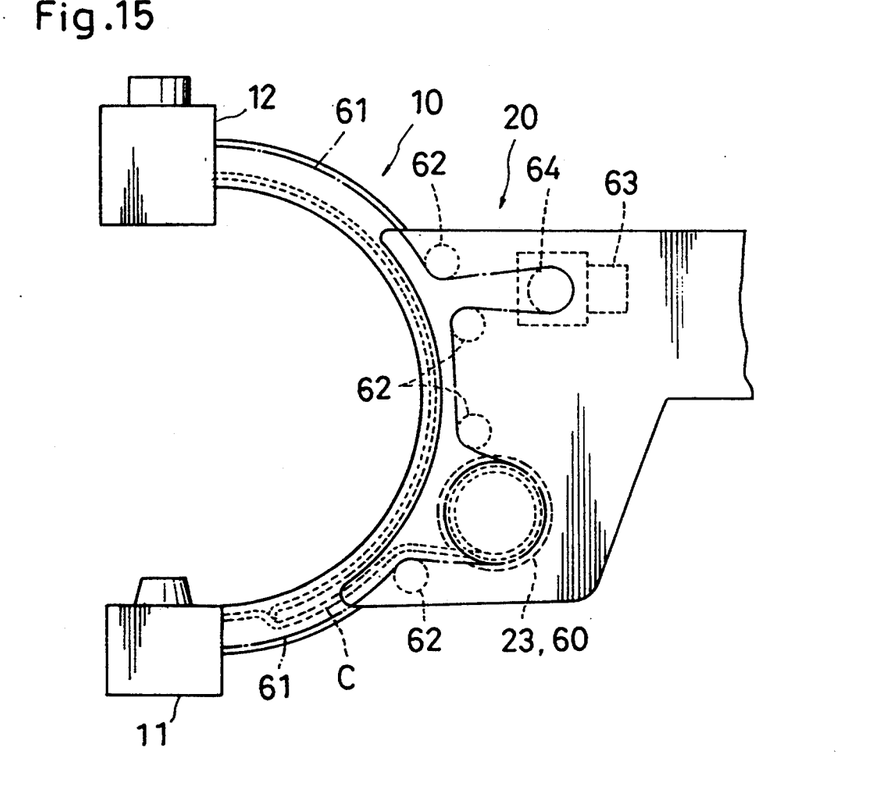
FIG. 15 is a front view of a principal portion of a third embodiment.

As shown in FIG. 15, the drum drive device in this embodiment includes a sprocket 60 connected to a take-up drum 23 to be rotatable therewith, a chain 61 engaged with the sprocket 60 and having opposite ends thereof guided by the outer periphery of the square pipe 14 of the C-shaped arm 10 and secured to the opposite ends of the arm 10, a plurality of guide sprockets 62 for guiding the chain 61, and a drive sprocket 64 connected to a motor 63 for driving the C-shaped arm 10. The chain 61 is movable with rotation of the drive sprocket 64, to rotate the C-shaped arm 10 and sprocket 60. As a result, the cable C is taken up on the take-up drum 23 or drawn therefrom by a length corresponding to a rotating angle of the C-shaped arm 10.

The above chain and sprockets may be replaced with a toothed belt and toothed pulleys.

Fourth Embodiment

Figure 16:
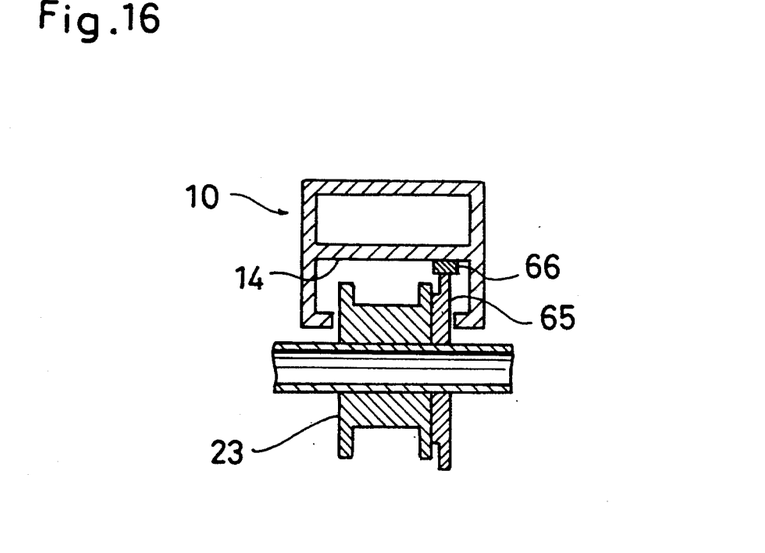
FIG. 16 is a view in vertical section of a principal portion of a fourth embodiment.

As shown in FIG. 16, the drum drive device in this embodiment includes a pinion 65 connected to a take-up drum 23 to be rotatable therewith, and a rack 66 fixed to the outer periphery of the square pipe 14 of the C-shaped arm 10 and engaged with the pinion 65. The pinion 65 engaged with the rack 66 is rotatable with rotation of the drive sprocket 64, whereby the cable C is taken up on the take-up drum 23 or drawn therefrom by a length corresponding to a rotating angle of the C-shaped arm 10.

The above pinion 65 and rack 66 may be replaced with a friction wheel.

Fifth Embodiment

Figure 17:
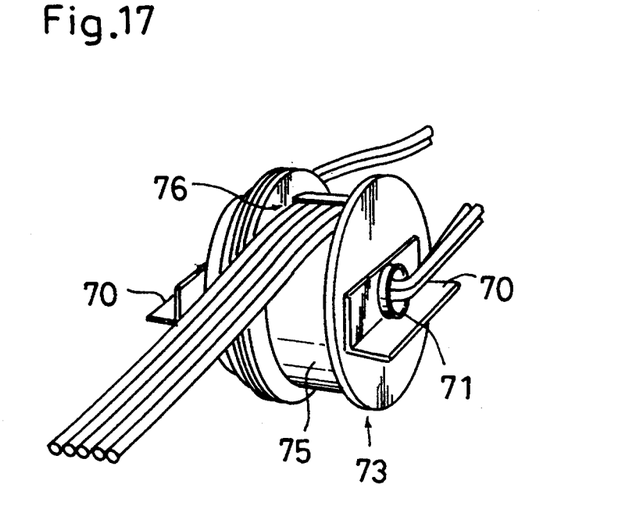
FIG. 17 is a perspective view of a take-up drum in a fifth embodiment.
Figure 18:
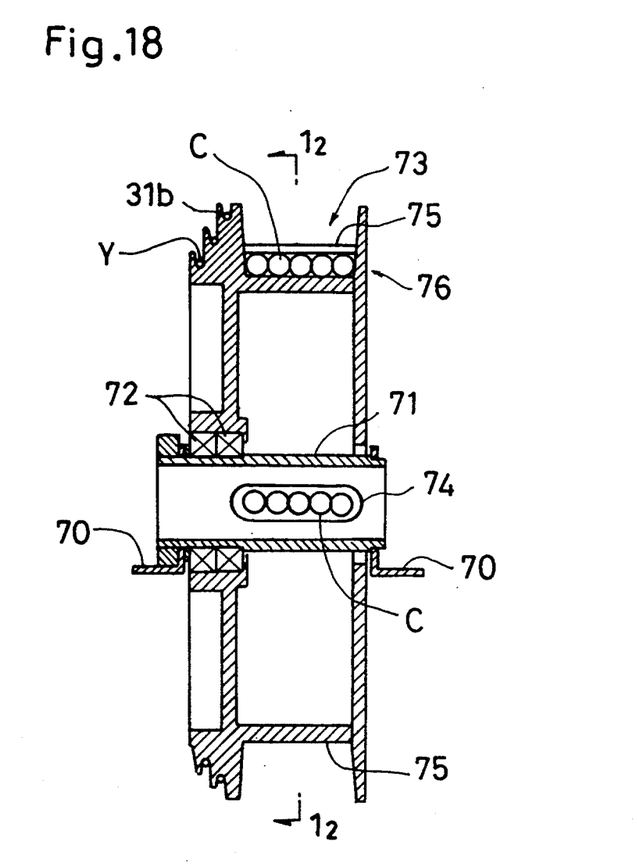
FIG. 18 is a view in vertical section of the take-up drum shown in FIG. 17.
Figure 19:
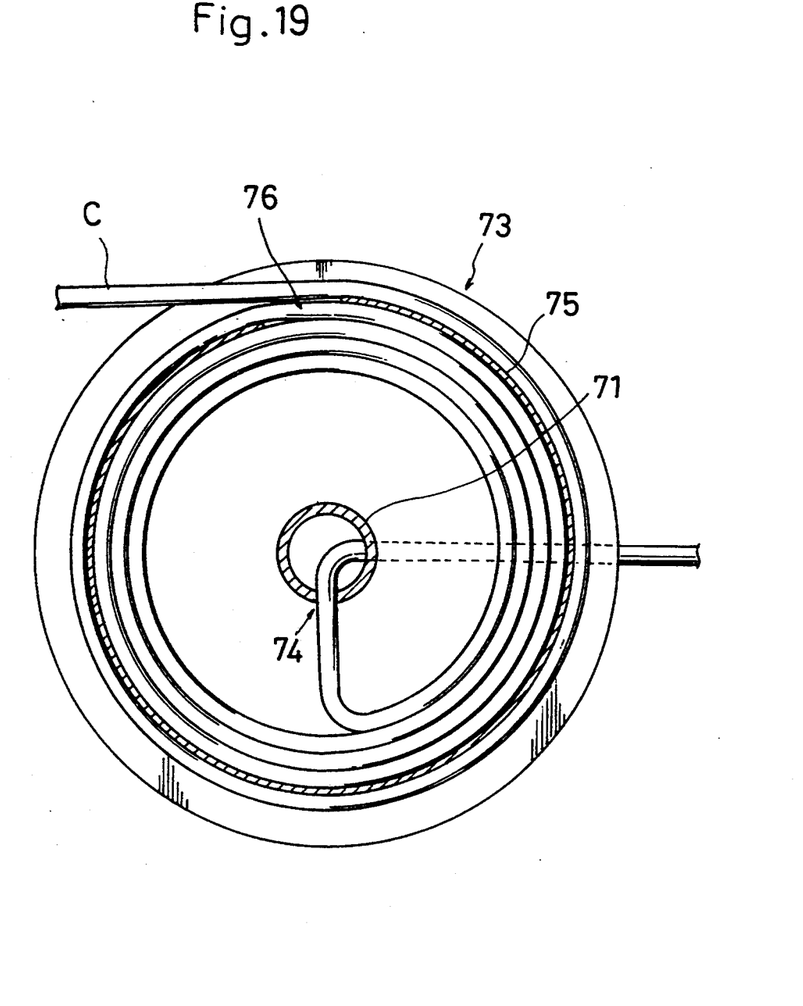
FIG. 19 is a section taken on line $1_{2l}$—$1_2$ of FIG. 17.

A principal portion of a radiographic apparatus in a fifth embodiment will be described with reference to FIGS. 17 through 19.

The arm holder 20 has a hollow shaft 71 attached thereto through a pair of brackets 70. The hollow shaft 71 rotatably supports a hollow take-up drum 73 through a pair of bearings 72. The take-up drum 73 defines a cable guide groove 75 having a width corresponding to a row of cables C to take up the row of cables C in an overlapping state. The cable guide groove 75 includes an intake bore 76 for introducing the cables C into the interior of the take-up drum 73. The intake bore 76 and the interior of the take-up drum 73 constitute a cable introducing section. As in the preceding embodiments, the hollow shaft 71 defines a through bore 74 for leading the cables C to the interior thereof.

The cables C guided by the outer periphery of the C-shaped arm 10 extend through the intake bore 76 of the cable guide groove 75 to the interior of the take-up drum 73, where the cables C are loosely wound several times. The cables C wound several times inside the take-up drum 73 are led by way of the through bore 74 to the interior of the hollow shaft 71, as in the preceding embodiments. Then, the cables 71 extend from one end of the hollow shaft 71 to the main body 50 of the apparatus.

In the first to fourth embodiments described hereinbefore, the hollow shaft 22 is connected to the take-up drum 23 to be rotatable therewith. Consequently, the cable C extending outward from the hollow shaft 22 is repeatedly subjected to torsional stress. This is undesirable for the cable C. In this embodiment, however, the hollow shaft 71 is stationary and causes no torsional stress on the cables C extending outward therefrom. On the other hand, a rotational displacement of the take-up drum 73 relative to the hollow shaft 71 is absorbed by resultant variations in a winding diameter of the cables C loosely wound inside the take-up drum 73. In this instance, only minimal stress is applied to the cables C without causing any mechanical deterioration thereof.

A pulley 31b, as in the second embodiment described hereinbefore, is connected to one side of the take-up drum 73. The take-up drum 73 is rotatable by the same drum drive device as in the second embodiment, to take up the cables C in the cable guide groove 75 or to allow the cables C to be drawn from the cable guide groove 75.

It will be appreciated that this invention is applicable also to other types of radiographic apparatus, such as one having a C-shaped arm supported by an arm holder suspended from a ceiling.

The present invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus comprising:
a C-shaped arm for supporting an X-ray tube at one end thereof and image receiving means at the other end;
an arm holder for slidably supporting said C-shaped arm for rotation about a center of an arc thereof;
a hollow shaft supported in said arm holder to extend substantially parallel to an axis of said center;
a take-up drum supported on said hollow shaft;
drum drive means responsive to rotation of said C-shaped arm to rotate said take-up drum; and
a plurality of cables connected to said X-ray tube and said image receiving means, respectively, and gathered into a bundle adjacent one of said X-ray tube and said image receiving means, said bundle being guided by an outer periphery of said C-shaped arm to be wound on said take-up drum, and extending through said take-up drum and said hollow shaft into and then out of said hollow shaft.

2. A radiographic apparatus as defined in claim 1, wherein said hollow shaft is rotatably supported in said arm holder, said take-up drum being rotatable with said hollow shaft about a common axis, said drum drive means including a pulley rotatable with said take-up drum about said common axis, and a wire wound on said pulley and having opposite ends thereof guided by said outer periphery of said C-shaped arm and secured to opposite ends of said C-shaped arm, said wire being wound on said pulley with a radius corresponding to a winding radius of said bundle on said take-up drum.

3. A radiographic apparatus as defined in claim 1, wherein said hollow shaft is rotatably supported in said arm holder, said take-up drum being rotatable with said hollow shaft about a common axis, and defining a cable guide groove having a width corresponding to a thickness of said bundle to take up said bundle in overlapping coils, said drum drive means including a pulley rotatable with said take-up drum about said common axis, and a wire having one end thereof secured to said pulley and the other end guided by said outer periphery of said C-shaped arm and secured to one end of said C-shaped arm, said pulley defining a wire guide groove in form of a conical spiral so that said wire is wound on said pulley with radii corresponding to radii of said bundle wound in overlapping coils on said take-up drum.

4. A radiographic apparatus as defined in claim 1, wherein said hollow shaft is rotatably supported in said arm holder, said take-up drum being rotatable with said hollow shaft about a common axis, said drum drive means including a sprocket rotatable with said take-up drum about said common axis, and a chain engaged with said sprocket and having opposite ends thereof guided by said outer periphery of said C-shaped arm and secured to opposite ends of said C-shaped arm, said chain being wound on said sprocket with a radius corresponding to a winding radius of said bundle on said take-up drum.

5. A radiographic apparatus as defined in claim 1, wherein said hollow shaft is rotatably supported in said arm holder, said take-up drum being rotatable with said hollow shaft about a common axis, said drum drive means including a pinion rotatable with said take-up drum about said common axis, and a rack engaged with said pinion and fixed to said outer periphery of said C-shaped arm.

6. A radiographic apparatus as defined in claim 1, wherein said hollow shaft is fixed to said arm holder, said take-up drum being rotatably supported on said hollow shaft, and defining a cable guide groove having a width corresponding to a thickness of said bundle and a cable introducing section formed between said cable guide groove and said hollow shaft for winding said bundle a plurality of times to take up said bundle in overlapping coils, said drum drive means including a pulley rotatable with said take-up drum about a common axis, and a wire having one end thereof secured to said pulley and the other end guided by said outer periphery of said C-shaped arm and secured to one end of said C-shaped arm, said pulley defining a wire guide groove in form of a conical spiral so that said wire is wound on said pulley with radii corresponding to radii of said bundle wound in overlapping coils in said take-up drum.

* * * * *